United States Patent
Neto et al.

(10) Patent No.: US 10,052,341 B2
(45) Date of Patent: Aug. 21, 2018

(54) METHOD FOR PREPARING AN ANTHELMINTIC COMPOSITION, ANTHELMINTIC COMPOSITION, VETERINARY TREATMENT METHOD AND ANTHELMINTIC TREATMENT METHOD

(71) Applicant: OURO FINO SAUDE ANIMAL PARTICIPACOES SA, Cravinhos (BR)

(72) Inventors: Dolivar Coraucci Neto, Sertaozinho (BR); Maira Neto Zampier, Ribeirao Preto (BR); Rodrigo Caetano Monti Guedes, Cajuru (BR)

(73) Assignee: OURO FINO SAUDE ANIMAL PARTICIPACOES SA, Sao Paulo (BR)

( * ) Notice: Subject to any disclaimer, the term of this patent is extended or adjusted under 35 U.S.C. 154(b) by 0 days.

(21) Appl. No.: 15/101,910

(22) PCT Filed: Dec. 4, 2014

(86) PCT No.: PCT/BR2014/000426
§ 371 (c)(1),
(2) Date: Jun. 4, 2016

(87) PCT Pub. No.: WO2015/081401
PCT Pub. Date: Jun. 11, 2015

(65) Prior Publication Data
US 2016/0303157 A1   Oct. 20, 2016

(30) Foreign Application Priority Data

Dec. 5, 2013 (BR) ............................ 102013031277

(51) Int. Cl.
| A61K 31/7048 | (2006.01) |
| A61K 31/4184 | (2006.01) |
| A61K 31/365 | (2006.01) |
| A61K 9/00 | (2006.01) |
| A61K 47/32 | (2006.01) |
| A61K 47/20 | (2006.01) |
| A61K 47/10 | (2017.01) |
| A61K 47/22 | (2006.01) |

(52) U.S. Cl.
CPC ........ *A61K 31/7048* (2013.01); *A61K 9/0019* (2013.01); *A61K 31/365* (2013.01); *A61K 31/4184* (2013.01); *A61K 47/10* (2013.01); *A61K 47/20* (2013.01); *A61K 47/22* (2013.01); *A61K 47/32* (2013.01)

(58) Field of Classification Search
CPC .............. A61K 31/7048; A61K 31/365; A61K 31/4184
See application file for complete search history.

(56) References Cited

U.S. PATENT DOCUMENTS

| 2007/0042013 A1* | 2/2007 | Soll ...................... A61K 9/0019 424/405 |
| 2007/0128239 A1* | 6/2007 | Hayes .................. A61K 9/0095 424/405 |
| 2012/0277175 A1 | 11/2012 | Neto et al. |

FOREIGN PATENT DOCUMENTS

| CN | 1839864 A | 10/2006 |
| CN | 102258529 A | 11/2011 |
| CN | 102440996 A | 5/2012 |
| WO | 2007068073 A2 | 6/2007 |
| WO | 2011143479 A1 | 11/2011 |

OTHER PUBLICATIONS

English machine translation of CN 102258529, EPO website, http://translationportal.epo.org/, accessed online on Oct. 27, 2017 (Year: 2017).*
Niazi, S.K., Handbook of Pharmaceutical Manufacturing Formulations: Liquid Products, 2004, CRC Press, vol. 3, p. 70 and 71. (Year : 2004).*
English language abstract for CN 1839864 A (2006).
English language abstract of CN 102258529 A (2011).
English language abstract of CN 102440996 A (2012).
International Search Report for PCT/BR2014/000426 dated Mar. 9, 2015.

* cited by examiner

*Primary Examiner* — Jonathan S Lau
(74) *Attorney, Agent, or Firm* — Caesar Rivise, PC

(57) ABSTRACT

The present invention relates to an injectable anthelmintic composition of avermectin and basic albendazole sulfoxide for combatting parasites that infest animals. The invention further contemplates a specific method that allows the stable association of avermectin and basic albendazole sulfoxide.

9 Claims, No Drawings

METHOD FOR PREPARING AN ANTHELMINTIC COMPOSITION, ANTHELMINTIC COMPOSITION, VETERINARY TREATMENT METHOD AND ANTHELMINTIC TREATMENT METHOD

INVENTION FIELD

The present invention refers to an injectable anthelmintic composition of avermectins and albendazole sulfoxide base for use to fight parasites that attack animals. The invention also includes a specific process that provides a stable association of avermectins and albendazole sulfoxide base.

BASE FOR THE INVENTION

Helminthiasis is a widely-occurring disease that affects several animal types, causing economic losses for their breeders. Cattle, sheep, goats, and horses are animals particularly susceptible to such diseases. Animal infection by helminths is deemed as the main cause for decrease in herd productivity and for herd morbidity and mortality.

Among the methods for endoparasite control, the most used one keeps being chemical. However, anthelmintic resistance (phenomenon occurring when an active principle cannot keep the same efficacy against parasites) has led to the need for associations or combinations of anthelmintic active principles with different mechanisms of action, aiming to improve the efficacy of each single drug, even in preventing parasitic resistance.

The use of anthelmintic associations or combinations implies that such products are applied together and thus that the individuals of the parasitic population are simultaneously exposed to more than one active principle. Nevertheless, the interaction of two different actives with different physical-chemical feature is still a challenge in the technical field.

There are a myriad of anthelmintic products of different pharmacological classes in the market. The pharmacological class of benzimidazoles is mainly characterized by albendazole. Another concerning chemical class is macrocyclic lactones, comprising avermectins.

However, the greatest problem associated to a benzimidazole-containing formulation, especially containing albendazole (ABZ), is its poor solubility in aqueous solution, which leads to its low and irregular bioavailability in animals.

The low water-solubility of benzimidazoles limits the commercially available formulation type, which is a suspension, paste, or granule for oral or intraruminal administration in most times.

Trying to overcome such issue, injectable solution-type formulations containing albendazole sulfoxide, also known as ricobendazole (RBZ) were developed and are widely commercialized.

Ricobendazole is the albendazole sulfoxide derivative, the main active metabolite of albendazole, used for treating parasitic disease in humans and animals. Albendazole sulfoxide can be found as a free base or as a salt as albendazole sulfoxide hydrochloride.

Injectable formulations stable as solution and containing albendazole sulfoxide hydrochloride are only likely to be formulated in a very low pH. Such condition makes the administration by subcutaneous likely to be precipitated at the injection site and to cause pain; furthermore, such formulations are incompatible with the avermectin used in the formulation under development, which is unstable in acid pH.

The application for patent BR P10619620 (WO2007/067470) describes an oral composition of a benzimidazole and a macrocyclic lactone, with only the use of triclabendazole and moxidectin being used as example. The composition formulation is a mixture of one or more surfactants, a water-miscible solvent (optionally an oil), triclabendazole, and moxidectin.

The application for patent BR P10316187 (WO2004043445) describes an aqueous micellar formulation, comprising a first ingredient selected from water-insoluble benzimidazoles and salicylanilides combined with a macrocyclic lactone (second active ingredient). The formulation contains tensoactives, used as formulation stabilizers, and also contains water-miscible solvents and water.

However, no known injectable association or formulation in the state of the art containing avermectin and albendazole sulfoxide presents desirable stability and efficacy, besides low local reaction.

INVENTION SUMMARY

The present invention presents an anthelmintic composition of an avermectin and albendazole sulfoxide base for use in fighting parasites that attack animals.

Additionally, the present invention includes a specific process that enables a stable association of avermectins and albendazole sulfoxide.

More particularly, the composition of the present invention proposes an injectable suspension of avermectins and albendazole sulfoxide, where albendazole is used as a free base.

DETAILED DESCRIPTION OF THE INVENTION

The first objective of the present invention is to provide an anthelmintic composition of an avermectin and albendazole sulfoxide as free base for fighting parasites that attack animals. Such composition, presented as an injectable suspension, is stable and efficient in animals.

Other objective of the present invention is to present a process that enables a stable association of an avermectin and albendazole sulfoxide base. The process of the present invention consists in adding a partial quantity of albendazole sulfoxide as free base in a mixture of solvents under heating, homogenizing the resulting mixture, cooling the homogenized mixture, and adding the total quantity of avermectin. Then, a permeation agent and a viscosity agent are added to the formulation containing the partial quantity of albendazole sulfoxide base and the total quantity of avermectin, obtaining a solution. The last step of the present process is the addition of the remaining quantity of albendazole base, followed by the homogenization of the final suspension.

By the invention process, it is possible to obtain a stable anthelmintic composition of avermectin and albendazole, even combining two actives with different mechanisms of action and physical-chemical features: macrocyclic lactones (represented by the avermectin) and benzimidazoles (represented by the albendazole sulfoxide base).

As already previously mentioned here, the low water-solubility of the benzimidazoles is responsible for the limited number of commercially available formulations, basically suspensions, pastes, or granules for oral or intraruminal administration.

Trying to overcome the lack in the art of stable and efficient compositions, the present invention proposes injectable solution-type formulations containing albendazole sulfoxide as free base.

Albendazole sulfoxide is the main active metabolite, a product of the microsomal oxidative metabolism of albendazole in the liver. The presence of the oxygen atom bound to sulfur in the albendazole sulfoxide (S=O) increases its water-solubility (67 µg/mL in pH 5) compared to the albendazole molecule (—S—) (0.53 µg/mL in pH 5).

After oral or ruminal administration, the rumen acts as a reservoir for the drug, enabling a prolonged release of small active quantities into the abomasum, where the drug will be dissolved in a lower pH and will be released to be absorbed in the intestine.

The subcutaneous administration of an albendazole sulfoxide formulation also enables a prolonged release effect. Considering that benzimidazoles are weak bases ($pK_a$ 6.8-7.8) and are only soluble in low pH, the administration of a solution by subcutaneous route in a region with pH 6.0 (such as the animal skin) might favor the drug precipitation at the application site, promoting slow absorption and sustained plasma concentrations.

Yet, the low pH needed for obtaining soluble albendazole sulfoxide, when administered by subcutaneous route, may cause lesions such as abscesses and edemas at the application site. Furthermore, the avermectin also used in the referred formulation is degraded in acid pH, making the association of the actives in solution incompatible.

Thus, the present invention proposes an injectable suspension of avermectin and albendazole sulfoxide as free base, without using the hydrochloride salt form or any other corresponding salt type, with no need for acidifying the medium, and with the advantages of the subcutaneous route, such as easy application and prolonged release, besides lower local irritation.

The disadvantage of the poor albendazole solubility and of the pH difference between actives is solved by the present process by the partial solubilization of such active in an organic carrier.

Therefore, a process for obtaining a composition according to the present invention is presented, comprising the following steps:

(a) adding about 40%-60% of albendazole free base to a mixture of organic solvents, with such mixture being previously heated at a temperature range between 55-75° C.;

(b) homogenizing the mixture by using mechanical agitation for about 20-40 minutes until full solubilization;

(c) cooling the homogenized mixture down to 30-40° C.;

(d) adding the total quantity of avermectin in the mixture cooled down in step (c);

(e) homogenizing the mixture obtained in step (d) by mechanical agitation for about 10-20 minutes up to its full solubilization, obtaining a solution;

(f) adding a viscosity agent and applying mechanical agitation up to the full homogenization of the mixture;

(g) adding a permeation agent and homogenizing; and (h) adding the remaining quantity of albendazole sulfoxide base, and homogenizing the final suspension.

The organic solvents used in the present invention may be selected in a group consisting of acetone, acetonitrile, benzyl alcohol, butyl alcohol, ethyl alcohol, isopropyl alcohol, methyl alcohol, benzyl benzoate, butyl diglycol, butyrolactone, N-dimethylacetamide, dimethylformamide, dimethyl sulfoxide, diethyl phthalate, diethylene glycol monoethyl ether, dipropylene glycol monomethyl ether, ethylene glycol, ethylene glycol monoethyl ether, methyl ester, glyceroformol, hexylene glycol, isopropanol, polyethylene glycol, propylene carbonate, propylene glycol, 2-pyrrolidone, N-methyl-2-pyrrolidone, N-methylformamide, triacetin, and medium-chain triglycerides.

The viscosity agents used in the present invention may be selected among carboxymethyl cellulose derivatives, polyvinylpyrrolidone derivatives, vinylpyrrolidone and vinyl acetate copolymers, macrogol derivatives, glycerin, propylene glycol, and sorbitol.

The permeation agents used in the present invention are selected among benzyl alcohol, butyl alcohol, ethyl alcohol, isopropyl alcohol, methyl alcohol, dimethyl sulfoxide, diethylene glycol monoethyl ether, dipropylene glycol monomethyl ether, ethylene glycol, and ethylene glycol monoethyl ether.

The present invention will be now defined referring to the following examples, which must not be interpreted as limiting the invention scope.

Example 1: Preparation of Injectable Formulations

The formulations of the present invention were obtained according to steps (a) to (h) of the process previously described here. A total of 40% of albendazole free base 10.0% w/v in a mixture of DMSO 40.0% w/v and N-methyl-pyrrolidone q.s. previously heated at a temperature between 65-70° C. was added. Then, the resulting mixture was homogenized and cooled down to about 30° C. The total quantity of avermectin 0.8% w/v was added to the mixture, followed by its solubilization, obtaining a solution. Glycerin 10.0% w/v was added, the solution was homogenized, and then 5.0 mL of ethyl alcohol were added. An addition of 60% of albendazole sulfoxide base was added, and the mixture was homogenized, obtaining the final suspension.

It was possible to obtain several formulations by the invention process. The tested formulations are presented in the Tables below.

TABLE 1

Ivermectin-containing formulation

| Ingredient | Percentile (%) | Ingredient Function |
|---|---|---|
| Albendazole sulfoxide base | 7.5-12.5 | Active ingredient |
| Ivermectin | 1.0-5.0 | Active ingredient |
| DMSO | 30.0-50.0 | Solvent |
| Ethyl alcohol | 1.0-12.5 | Permeation agent |
| Glycerin | 7.5-12.5 | Viscosity agent |
| N-methyl-2-pyrrolidone | q.s. 100 mL | Carrier |

TABLE 2

Abamectin-containing formulation

| Ingredient | % w/v | Ingredient Function |
|---|---|---|
| Albendazole sulfoxide base | 7.5-12.5 | Active ingredient |
| Abamectin | 1.0-5.0 | Active ingredient |
| DMSO | 30.0-50.0 | Solvent |
| Anhydrous ethyl alcohol | 1.0-12.5 | Permeation agent |
| Glycerin | 7.5-12.5 | Viscosity agent |
| N-methyl-2-pyrrolidone | q.s. 100 mL | Carrier |

TABLE 3

Moxidectin-containing formulation

| Ingredient | % w/v | Ingredient Function |
|---|---|---|
| Albendazole sulfoxide base | 7.5-12.5 | Active ingredient |
| Moxidectin | 1.0-5.0 | Active ingredient |
| DMSO | 30.0-50.0 | Solvent |
| Anhydrous ethyl alcohol | 1.0-12.5 | Permeation agent |
| Glycerin | 7.5-12.5 | Viscosity agent |
| N-methyl-2-pyrrolidone | q.s. 100 mL | Carrier |

TABLE 4

Eprinomectin-containing formulation

| Ingredient | % w/v | Ingredient Function |
|---|---|---|
| Albendazole sulfoxide base | 7.5-12.5 | Active ingredient |
| Eprinomectin | 1.0-5.0 | Active ingredient |
| DMSO | 30.0-50.0 | Solvent |
| Anhydrous ethyl alcohol | 1.0-12.5 | Permeation agent |
| Glycerin | 7.5-12.5 | Viscosity agent |
| N-methyl-2-pyrrolidone | q.s. 100 mL | Carrier |

TABLE 5

Doramectin-containing formulation

| Ingredient | % w/v | Ingredient Function |
|---|---|---|
| Albendazole sulfoxide base | 7.5-12.5 | Active ingredient |
| Doramectin | 1.0-5.0 | Active ingredient |
| DMSO | 30.0-50.0 | Solvent |
| Anhydrous ethyl alcohol | 1.0-12.5 | Permeation agent |
| Glycerin | 7.5-12.5 | Viscosity agent |
| N-methyl-2-pyrrolidone | q.s. 100 mL | Carrier |

The formulations of the present invention were obtained according to steps (a) to (h) of the process previously described here.

Example 2: Anthelmintic Efficacy Study

An anthelmintic efficacy study was conducted with formulation 1 when applied by subcutaneous routes in cattle naturally infected with gastrointestinal nematodes, besides possible local reactions.

Seven Nelore heifers in good nutritional and health status, aged from 10 to 19 months old and naturally infected by gastrointestinal helminths were used. Only animals with egg count per gram of feces higher than 150 were included in the study, according to COLES et al. (1992).

The formulation administration was performed by subcutaneous route in the side of the neck region, at a single dose, following a dosage of 1 mL for every 40 kg body weight, using sterile and disposable needles and syringes.

Fecal samples were collected from each animal for coproparasitological evaluation by Gordon & Whitlock and Roberts & O'Sullivan methods fourteen days (D-14) before the treatment and, besides that, there was an observation for the presence of possible previous lesions on the animals (for determining the side to administer the medicine) (UENO & GONÇALVES, 1998). Only animals presenting egg counts per gram of feces equal to or higher than 150 were included in the trial. Parasitism by gastrointestinal nematodes was very disseminated by animals, with mixed infection by genuses *Haemonchus, Cooperia*, and *Oesophagostomum*, in ratios of 62%, 34%, and 4%, respectively. The general mean of egg count per gram of feces was 433.33.

The animals were weighed on mechanical scale for determining the medicine volume on Day 0 and, besides that, fecal collection and observation for preexistent lesions.

After the treatment, the fecal samples were collected on D+14 again for repeating the fecal tests. The application sites were observed for detecting any adverse event related to the administration of the invention medicine. If a tissular reaction was seen, the lesion diameter was gauged by a precision caliper rule.

Along the whole trial period, the elimination of eggs in the animal feces was monitored by quantitative methods. The egg count per gram of feces obtained in the collections referring to D-14, D0, and D+14 provided the results described in Table 2. The numbers of eggs of nematodes were determined in the feces by the egg count technique (Gordon & Whitlock (1939) (J. Council for Scientific and Industrial Res., 12, 50).

TABLE 6

Individualized detailing of the results of egg count per gram (EPG) by the Gordon & Whitlock method

| Animal | D −14 (EPG) | D 0 (EPG) | D +14 (EPG) |
|---|---|---|---|
| Animal 4467 | 700 | 1000 | 50 |
| Animal 4446 | 250 | 900 | 0 |
| Animal 4483 | 150 | 100 | 0 |
| Animal 4400 | 300 | 150 | 0 |
| Animal 9 | 300 | 300 | 0 |
| Animal 4501 | 1000 | 550 | 0 |
| Animal 4462 | 350 | 500 | 50 |
| Mean* | 435.71 | 500.0 | 14.28 |

*Arithmetic Mean

The treatment efficacy, only based on the EPG value and determined according to an equation proposed by Wood et al. (1995), was 97.14%. The local reactions at any animal are described in detail in Table 3.

TABLE 7

Standard of local reactions seen on the animals in the trial groups.

| Animal | Diameter of local reaction |
|---|---|
| 4467 | NDN |
| 4446 | 55 mm |
| 4483 | NDN |
| 4400 | 48 mm |
| 9 | NDN |
| 4501 | NDN |
| 4462 | NDN |

It is seen from the results in Table 6 that the composition of the present invention presented anthelmintic efficacy. Furthermore, Table 7 shows that the composition had not developed local reactions when applied by subcutaneous route.

It is important to highlight that it is possible to provide a final composition with specific concentrations by the process of the present invention and the use of albendazole sulfoxide base.

The composition of the present invention is particularly destined to veterinary use, and the typical animals include pets and farm livestock, particularly livestock and especially pigs, goats, horses, cattle, sheep, dogs, cats, and poultry.

The invention composition is efficient against helminthic endoparasites, particularly gastrointestinal nematodes, cestodes, and trematodes.

Though the preferable invention presentations have been described in detail, it is understood that obvious variations can be performed without going apart from the invention spirit and scope, such as defined in the attached claims.

Example 3: Evaluation of Stabilities of the Compositions with Avermectins

A visual evaluation test of precipitation was conducted for the formulations when only 40.0% of albendazole sulfoxide free base 10% w/v (corresponding to the soluble albendazole fraction), avermectins 3.2% w/v, DMSO 40.0% w/v, glycerin 10.0% w/v, and 4.0 mL of ethyl alcohol were added.

All compositions presented above were visually evaluated for observation for precipitates at the conditions of 40° C., room temperature (25° C.), and refrigerator (4° C. to 8° C.).

There was avermectin solubilization in five compositions. There was no precipitation in any formulation with 1 and 6 months of stability.

Though preferable invention presentations have been described in detail, it is understood that obvious variations may be performed without going apart from the invention spirit and scope, such as defined in the attached claims.

The invention claimed is:

1. A process to prepare an anthelmintic composition comprising the following steps:
   (a) heating a mixture of organic solvents to a temperature within the range of 55-75° C.;
   (b) adding about 40%-60% of a total anthelmintically effective amount of albendazole free base to the mixture of organic solvents;
   (c) homogenizing the mixture of organic solvents and albendazole free base by using mechanical agitation for about 20-40 minutes until full solubilization to provide a homogenized mixture;
   (d) cooling the homogenized mixture down to 30-40° C.;
   (e) adding an anthelmintically effective amount of avermectin to the homogenized mixture cooled down in step (c);
   (f) homogenizing the mixture obtained in step (d) by mechanical agitation for about 10-20 minutes up to its full solubilization, obtaining a solution;
   (g) adding from 7.5 to 12.5% w/v of a viscosity agent to the solution obtained in step (f), and applying mechanical agitation up to a full homogenization of the mixture;
   (h) adding from 1.0 to 12.5% w/v of a permeation agent and homogenizing; and
   (i) adding a remaining quantity of the total anthelmintically effective amount of albendazole sulfoxide base, and homogenizing the final suspension,
   wherein the avermectin in step (e) is added in an amount up to 5.0% w/v of the final suspension.

2. The process according to claim 1, wherein the organic solvents are selected from the group consisting of acetone, acetonitrile, benzyl alcohol, butyl alcohol, ethyl alcohol, isopropyl alcohol, methyl alcohol, benzyl benzoate, butyl diglycol, butyrolactone, N-dimethylacetamide, dimethylformarmide, dimethyl sulfoxide, diethyl phthalate, diethylene glycol monoethyl ether, dipropylene glycol monomethyl ether, ethylene glycol, ethylene glycol monoethyl ether, methyl ether, glyceroformol, hexylene glycol, isopropanol, polyethylene glycol, propylene carbonate, propylene glycol, 2-pyrrolidone, N-methyl-2-pyrrolidone, N-methyl-formamide, triacetin, and medium-chain triglycerides.

3. The process according to claim 1, wherein the viscosity agent is a member selected from the group consisting of carboxymethyl cellulose derivatives, polyvinylpyrrolidone derivatives, vinylpyrrolidone and vinyl acetate copolymers, macrogol derivatives, glycerin, propylene glycol, and sorbitol.

4. The process according to claim 1, wherein the permeation agent is a member selected from the group consisting of benzyl alcohol, butyl alcohol, ethyl alcohol, isopropyl alcohol, methyl alcohol, dimethyl sulfoxide, diethylene glycol monoethyl ether, dipropylene glycol monomethyl ether, ethylene glycol, and ethylene glycol monoethyl ether.

5. The process according to claim 1, wherein the quantity of albendazole free base to be added in step (b) is 40%.

6. The process according to claim 1, wherein the avermectin is a member selected from the group consisting of ivermectin, abamectin, moxidectin, eprinomectin, and doramectin.

7. The process according to claim 1, wherein the mixture of organic solvents comprise a mixture of dimethyl sulfoxide and N-methyl-2-pyrrolidone.

8. The process according to claim 1, wherein the viscosity agent is a member selected from the group consisting of macrogol derivatives, glycerin, propylene glycol, and sorbitol.

9. The process according to claim 1, wherein the permeation agent is a member selected from the group consisting of benzyl alcohol, butyl alcohol, ethyl alcohol, isopropyl alcohol and methyl alcohol.

* * * * *